(12) United States Patent
Stenger et al.

(10) Patent No.: US 6,485,928 B2
(45) Date of Patent: Nov. 26, 2002

(54) USE OF GRANULYSIN AS AN ANTIMICROBIAL AGENT

(75) Inventors: Steffen Stenger, Erlangen (DE); Robert L. Modlin, Sherman Oaks, CA (US); Dennis Alan Hanson, Mountain View, CA (US); Alan M. Krensky, Stanford, CA (US)

(73) Assignees: The Board of Trustees of the Leland Stanford Junior University, Palo Alto, CA (US); The Regents of the University of California, Palo Alto, CA (US)

( * ) Notice: Subject to any disclaimer, the term of this patent is extended or adjusted under 35 U.S.C. 154(b) by 152 days.

(21) Appl. No.: 09/185,245

(22) Filed: Nov. 3, 1998

(65) Prior Publication Data

US 2002/0044927 A1 Apr. 18, 2002

Related U.S. Application Data

(60) Provisional application No. 60/064,265, filed on Nov. 4, 1997.

(51) Int. Cl.$^7$ ............ A61K 35/14; G01N 33/574; G01N 33/53; G01N 33/569; G01N 33/554

(52) U.S. Cl. ............ 435/32; 424/534; 435/7.23; 435/7.24; 435/7.31; 435/7.32; 435/32; 435/33; 435/68.1; 435/174; 435/176; 435/177; 435/185; 435/183; 435/343; 435/803; 530/388.7; 530/389.6; 530/820; 935/33; 935/34

(58) Field of Search ............ 424/534; 435/7.23, 435/7.24, 7.31, 7.32, 32, 33, 68.1, 174, 176, 177, 182, 183, 343, 803; 530/388.7, 389.6, 820; 536/16.8, 23.7, 24.32; 935/33, 34

(56) References Cited

U.S. PATENT DOCUMENTS

4,994,369 A * 2/1991 Krensky et al. ............ 435/6
5,981,469 A * 11/1999 Anderson et al. ............ 514/2

FOREIGN PATENT DOCUMENTS

WO 92/06195 4/1992

OTHER PUBLICATIONS

Anderson et al. 1995, EMBO Journal, 14(8): 1615–1625.*
Miyakawa et al. 1996. Infection and Immunity. 64(3): 926–932.*
Pena et al. 1997. Immnunology. 9:117–125.*
Pena et al. 1997. J of Immunology. 158(6):2680–2687.*
Stenger et al. 1997. Science. 276: 1684–1687.*
Stenger et al. 1998. Science. 282: 121–125, 1995.*
Andersson, Mats, et al. "NK–lysin, A Novel Effector Peptide Of Cytotoxic T And NK Cells. Structure And cDNA Cloning Of the Porcine Form, Induction By Interleukin 2, Antibacterial And Antitumour Activity," *The EMBO Journal* (1995) vol. 14, No. (8):1615–1625.
Miyakawa, Yosuke, et al., "In Vitro Activity Of The Antimicrobial Peptides Human And Rabbit Defensins And Porcine Leukocyte Protegrin Against *Mycobacterium Tuberculosis*," *Infection and Immunity* (1996) vol. 64, No. (3):926–932.

(List continued on next page.)

*Primary Examiner*—Lynette R. F. Smith
*Assistant Examiner*—Ja-Na Hines

(57) ABSTRACT

The T cell activation marker, granulysin, is demonstrated to be an effective antimicrobial agent. It is used in vitro and in vivo to reduce the population of viable cells in a microbial population. Of particular interest is the use of the active fragment of human granulysin, or modified forms thereof, to treat bacterial infections.

18 Claims, 5 Drawing Sheets

OTHER PUBLICATIONS

Stenger, Steffen et al., "An Antimicrobial Activity Of Cytolytic T Cells Mediated By Granulysin," *Science* (1998) vol. 282:121–125.

Donlon, T.A., et al., "Localization Of The Human T Lymphocyte Activation Gene 519 (D2S69E) To Chromosome 2p12–q11," *Cytogent. Cell Genet.* (1990) vol. 53:230–231.

Genbank Accession No. X05044.

Genbank Accession No. X54101.

Jongstra, Jan, et al., "The Isolation And Sequence Of A Novel Gene From A Human Functional T Cell Line," *The Journal Of Experimental Medicine* (Mar. 1, 1997) vol. 165, No. (3):601–614.

Lowin, Bente, et al., "A Null Mutation In The Perforin Gene Impairs Cytolytic T Lymphocyte–And Natural Killer Cell–Mediated Cytotoxicity," *Proc. Natl. Acad. Sci. USA* (Nov. 1994) vol. 91:11571–11575.

Manning, William C., et al., "Genomic Structure And Alternative Splicing Of 519, A Gene Expressed Late After T Cell Activation," *The Journal Of Immunology* (Jun. 15, 1992) vol.148:4036–4042.

Peña, Susan V., et al., "Processing Subcellular Localizaion And Function Of 519 (Granulysin), A Human Late T Cell Activation Molecule With Homology To Small Lytic, Granule Proteins[1]," *The Journal Of Immunology* (Mar. 15, 1997) vol. 158, No. (6):2680–2688.

Peña, Susan V. and Krensky, Alan M., "Granlysin, A New Human Cytolytic Granule–Associated Protein With Possible Involvement In Cell–Mediated Cytotoxicity," *Immunology* (1997) vol. 9:117–125.

Podak, Eckhard, R., et al., "Structure, Function And Expression Of Murine And Human Perforin(Pl),"0 *Immunological Reviews* (1988) No. 103:203–211.

* cited by examiner

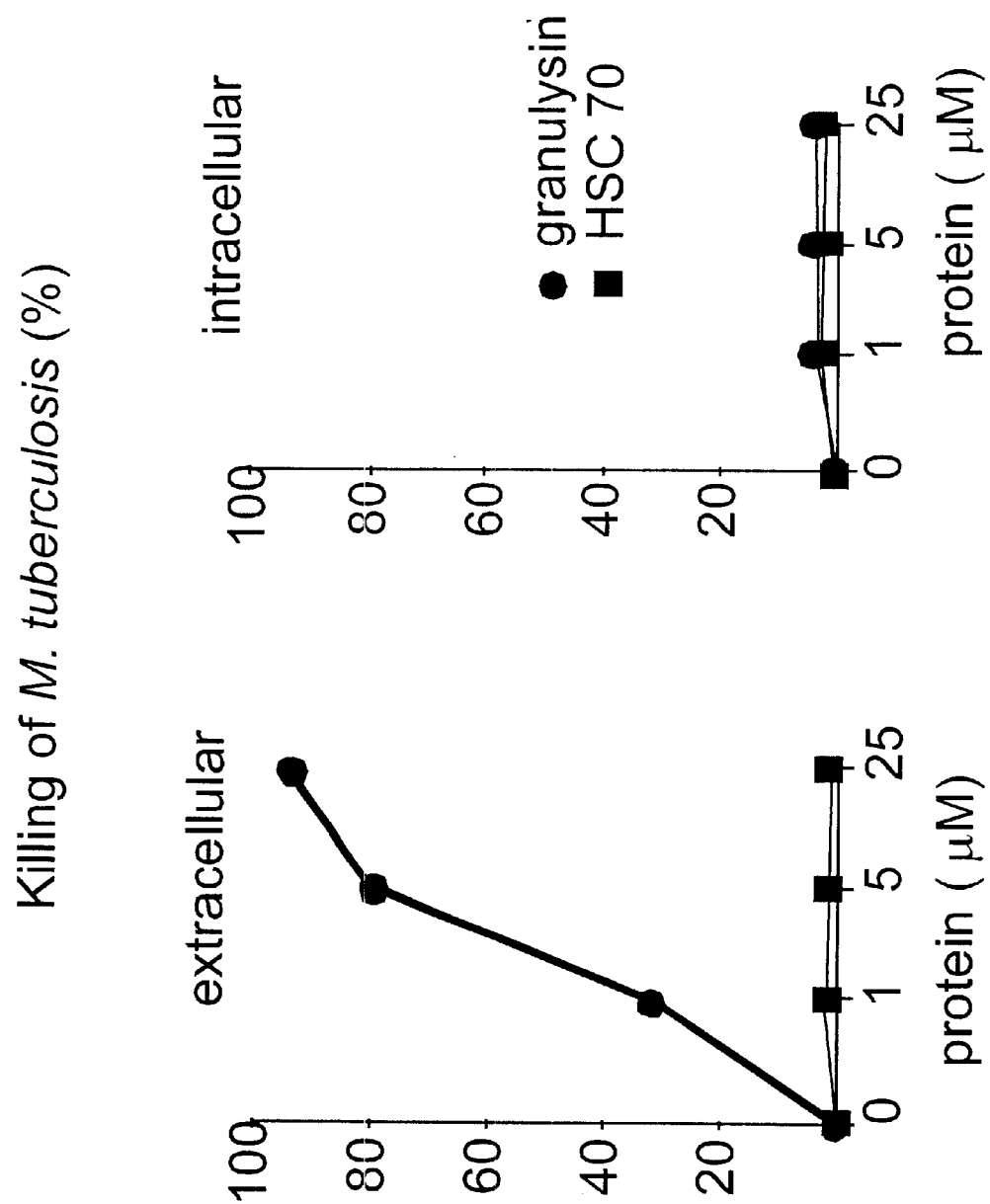

USE OF GRANULYSIN AS AN ANTIMICROBIAL AGENT

This application is related to U.S. provisional patent application Ser. No. 60/064,265 filed Nov. 4, 1997, and is incorporated herein by reference.

STATEMENT AS TO FEDERALLY SPONSORED RESEARCH

This invention was made with Government support under Grant no. DK35008, awarded by the National Institutes of Health. The Government may have certain rights in this invention.

INTRODUCTION

Background

It was not long ago that the war against microbial disease was thought to be won, through the use of antibiotics and vaccines. It is now seen that there remains much to be done in this field. Although antibiotics are a huge industry, totaling $22.9 billion in worldwide sales, there are still significant unmet clinical needs caused by growing bacterial resistance problems that require new antibacterial therapies.

A bacterial pathogen of major concern is *Mycobacterium tuberculae* (*M. tb.*). It is highly infectious, and treatment requires a long course of antibiotics. Frequently, patients fail to complete treatment, thereby selecting for antibiotic resistant bacteria. Significant reservoirs of virtually untreatable *M.tb.* are already present in some lesser developed parts of the world. It is expected that these will cause a pandemic in the future, unless improved therapies can be produced.

The mammalian immune system plays a key role in controlling the course of microbial infection in vivo. T cells play a pivotal role as regulators and effectors in the immune response. Cytolytic T cells (CTL) are directly involved in the lysis of foreign and virally infected cells. Two major types of T cell-mediated cytolysis have been well characterized. The regulated, directional release of cytoplasmic granule contents is a primary mechanism by which CTL and NK cells initiate the target cell death process. In addition, Fas-Fas ligand interaction mediates T-cell directed cytolysis.

Proteins present in cytoplasmic granules, including the pore-forming protein perforin, and a family of serine proteases called granzymes, have been implicated in granule mediated cytolysis. Interest in the precise mechanism of cytolysis has stimulated the search for additional molecules present on these highly specialized organelles. Early studies of cytolytic granules included density gradient purification and subsequent analysis, in which were observed low molecular weight proteins of unknown identity. It has recently been determined that one of the proteins present in granules is the late T cell activation marker, granulysin.

Many intracellular and extracellular pathogens meet their death within phagocytes. T cells contribute to antimicrobial defense by activating macrophages to kill the foreign invader. However, a microbicidal pathway by which T cells directly kill the pathogen has not been elucidated. Exploring the pathways by which microbes are eliminated in vivo is of great interest for the development of novel therapies and screening for novel antibiotics Relevant Literature U.S. Pat. No. 4,994,369 discloses the nucleotide and predicted amino acid sequence of the "519" protein, herein referred to as granulysin. The sequences of granulysin variants may be accessed from the Genbank and EMBL databases, with the accession number X05044 for the mRNA sequence of 519; EMBL accession X05044 for the encoded protein; and EMBL: locus HSNKG5, accession X54101 for the NKG5 splice variant.

The sequence and structure of the granulysin gene is discussed in Jongstra et al. (1987) *J. Exp. Med.* 165:601–614; Donlon et al. (1990) *Cytogenet. Cell Genet.* 53:230–231; and Manning et al. (1992) *J. Immunol.* 148:4036–4042.

The processing, sub-cellular localization and function of granulysin in cell-mediated cytotoxicity is discussed in Pena and Krensky (1997) *Sem. Immunol.* 9:117–125; and in Pena et al. (1997) *J. Immunol.* 158:2680–2688.

The structure, function and expression of human and murine perforin is discussed in Podack et al. (1988) *Immun. Rev.* 103:203–211. The role of perforin in cytolytic T cell killing is explored through the use of transgenic knock-outs in Lowin et al. (1994) *P.N.A.S.* 91:11571–11575.

SUMMARY OF THE INVENTION

Methods are provided for the use of granulysin protein as an antimicrobial agent. A pharmaceutical composition comprising granulysin as an active agent is administered to a patient suffering from a microbial infection, particularly bacterial infections. The protein is also effective at killing a variety of microbial organisms in vitro. Granulysin may be administered alone, or in combination with other bacteriocidal agents, e.g. perforin, antibiotics, etc. Such combined formulations are effective in killing *M. tb*. The administered granulysin may be one of the naturally occurring forms of the protein, or a synthetic variant derived therefrom. Granulysin mediated killing of microbes is also useful for modeling and screening novel antibiotics.

BRIEF DESCRIPTION OF THE DRAWINGS

FIGS. 3A and 3B are graphs depicting the killing of extracellular *M. tb.*, but not intracellular, by granulysin alone.

DESCRIPTION OF THE SPECIFIC EMBODIMENTS

Figure 1:
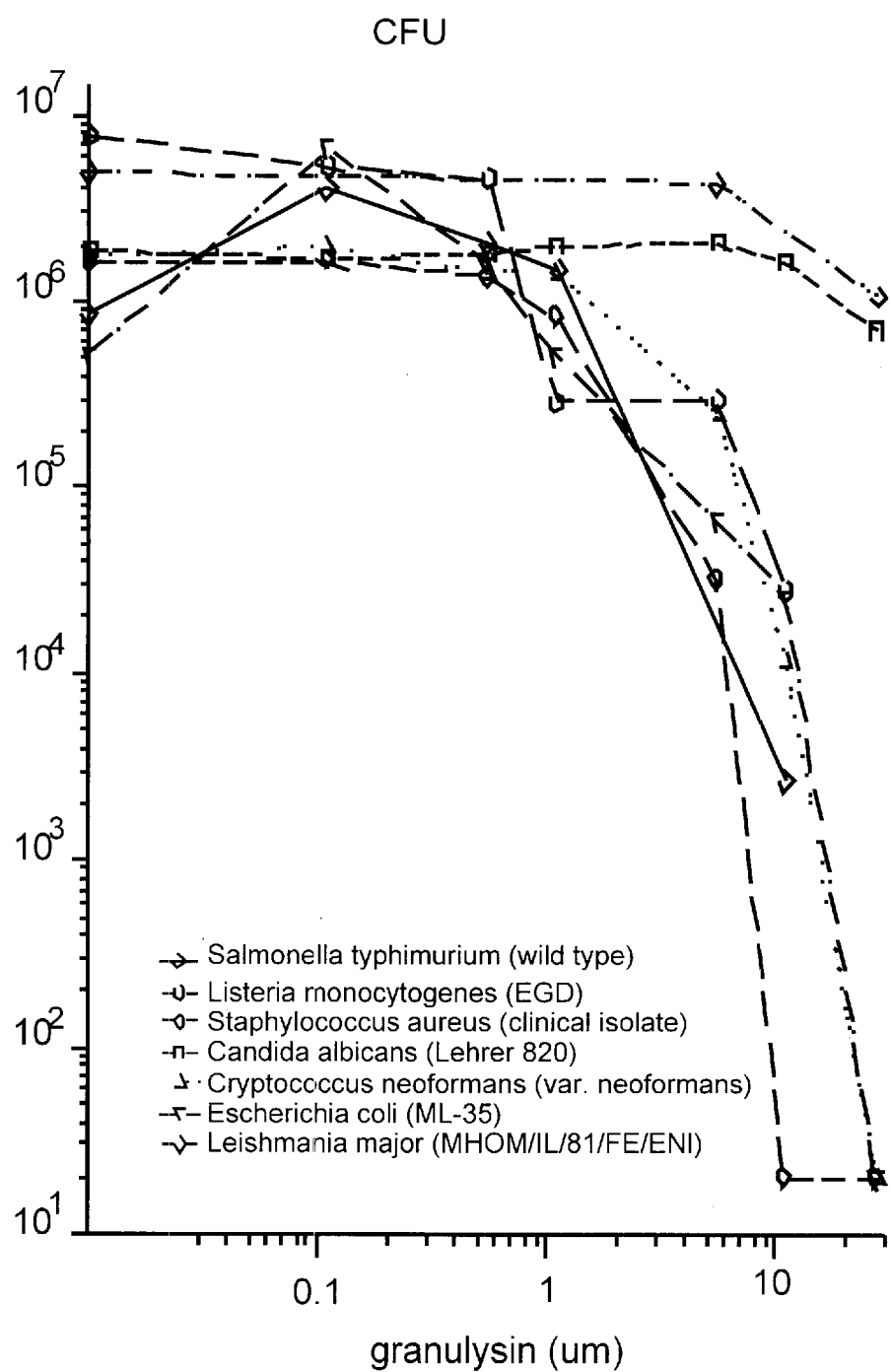
FIG. 1 is a graph depicting the killing of a variety of microbes by differing concentrations of granulysin.

Methods are provided for the use of granulysin as an antimicrobial agent. The protein is effective at killing a variety of microbial organisms in vitro and in vivo by direct microbicidal activity. Granulysin is administered alone or in combination with other active agents to a patient suffering from an infection, in a dose and for a period of time sufficient to reduce the patient population of microbial pathogens. A combined formulation of granulysin and perforin is provided, which is effective in killing intracellular *M. tb*. The presence of granulysin in CTL is shown to be a marker for T cell immunity against microbial pathogens.

There is a continuing need for new antimicrobial agents, particularly those that are effective in killing pathogens resistant to conventional antibiotics, e.g. *M. tb.* Granulysin is a protein that is involved in the natural pathways of resistance to microbial infection. The structure and activity of granulysin suggest that its action is unrelated to that of conventional antibiotics. It is therefore exceptionally useful as a clinical drug. The novel pathway also provides a useful model for drug screening, in the rational design of antimicrobial drugs.

The native forms of human granulysin provide a basis for further therapeutic development, by modification of the polypeptide structure to yield modified forms having altered biological and chemical properties. The native or modified forms are formulated in a physiologically acceptable carrier for therapeutic uses, or are otherwise used as an antimicrobial agent.

Detection of the presence of granulysin in a T cell population is indicative of protective immunity. Detection may be carried out by any convenient method, as known in the art. Suitable assays include RT-PCR, northern blotting and other assays for the presence of specific mRNA. Other assays are based on immunoreactivity, e.g. ELISA, RIA, immunohistochemistry, etc., or on functional assays, such as the ability to kill susceptible microbes.

Granulysin Compositions

For use in the subject methods, any of the native granulysin forms, modifications thereof, or a combination of one or more forms may be used. Shorter forms are generally preferable over longer. The granulysin sequence may be from any mammalian or avian species, e.g. primate sp., particularly humans; rodents, including mice, rats and hamsters; rabbits; equines, bovines, canines, felines; etc. Of particular interest are the human proteins. Generally, for in vivo use the granulysin sequence will have the same species of origin as the animal host. For in vitro use, any convenient species having high activity against the microbe being treated may be used.

There are several naturally occurring variants of human granulysin, resulting from three different spliced forms of mRNA, and from proteolytic processing of the primary polypeptide products. The amino acid sequence of the different forms are provided as follows:

| | |
|---|---|
| SEQ ID NO: 1 | 9 kD form, proteolysis product of P519 |
| SEQ ID NO: 2 | P519 |
| SEQ ID NO: 3 | P520 |
| SEQ ID NO: 4 | P522 |
| SEQ ID NO: 3, aa 16–145 | mature form of P520 (signal cleaved) |
| SEQ ID NO: 4, aa 16–172 | mature form of P522 (signal cleaved) |

The nucleic acid sequences encoding the above human granulysin polypeptides may be accessed from public databases as previously cited. Identification of non-human granulysins is accomplished by conventional screening methods of DNA libraries or biological samples for DNA sequences having a high degree of similarity to known granulysin sequences.

The sequence of the granulysin polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Deletions may further include larger changes, such as deletions of a domain or exon, providing for active peptide fragments of the protein. Other modifications of interest include epitope tagging, e.g. with the FLAG system, HA, etc. Such alterations may be used to alter properties of the protein, by affecting the stability, specificity, etc.

Techniques for in vitro mutagenesis of cloned genes are known. Examples of protocols for scanning mutations may be found in Gustin et al., *Biotechniques* 14:22 (1993); Barany, *Gene* 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press 1989, pp. 15.3–15.108; Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu *Anal Biochem* 177:120–4 (1989).

The protein may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. In this situation, the subject peptide will be bound to a lipid group at a terminus, so as to be able to be bound to a lipid membrane, such as a liposome.

When the granulysin is to be secreted, the coding sequence for the extracellular domain will be fused, in frame, with sequences that permit secretion, including a signal peptide. Signal peptides may be exogenous or native. The subject peptides may be PEGylated, where the polyethyleneoxy group provides for enhanced lifetime in the blood stream. The subject peptides may also be combined with other proteins, such as the Fc of an IgG isotype, which may be complement binding, with a toxin, such as ricin, abrin, diphtheria toxin, or the like, or with specific binding agents that allow targeting to specific moieties on a target cell. When the granulysin is to be expressed on the surface of the cell, the coding sequence for the extracellular domain will be fused, in frame, with sequences encoding a peptide that anchors the extracellular domain into the membrane and a signal sequence. Such anchor sequences include transmembrane domains from cell surface proteins, e.g. CD4, CD8, sIg, etc.

Where targeting is desired, the active domain of granulysin may be produced as a fusion protein with an antibody that is specific for a target cell of interest, thereby providing for an antimicrobial antibody composition. The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

The granulysin for use in the subject methods may be produced from eukaryotic or prokaryotic cells. Where the protein is produced by prokaryoticcells, it may be further processed by unfolding, e.g. heat denaturation, DTT reduction, etc. and may be further refolded, using methods known in the art. Both the reduced/unfolded (particularly the 9 kDa form), and the refolded forms of granulysin are active. The unfolded protein differs in some properties, e.g. it is capable of lysing red blood cells. Reduced granulysin is more lytic per fixed concentration, and exhibits a quicker lytic activity. Refolded granulysin, but not reduced granulysin, is inhibited by EDTA.

Methods of Use

Formulations of granulysin are administered to a host suffering from a microbial infection. Administration may be topical, localized or systemic, depending on the specific microorganism. Generally the dose of granulysin will be sufficient to decrease the microbial population by at least about 50%, usually be at least about 1 log, and may be 2 or more logs of killing. The compounds of the present invention are administered at a dosage that reduces the microbial population while minimizing any side-effects. It is contemplated that the composition will be obtained and used under the guidance of a physician for in vivo use. Combined formulations of granulysin with perforin are particularly useful for killing intracellular *M. tb*.

Granulysin is useful for in vitro formulations to kill microbes, particularly where one does not wish to introduce quantities of conventional antibiotics. For example, granulysin may be added to animal and/or human food preparations. Granulysin may be included as an additive for in vitro cultures of cells, to prevent the overgrowth of microbes in tissue culture.

The susceptibility of a particular microbe to killing with granulysin may be determined by in vitro testing, as detailed in the experimental section. Typically a culture of the microbe is combined with granulysin at varying concentrations for a period of time sufficient to allow the protein to act, usually between about one hour and one day. The viable microbes are then counted, and the level of killing determined.

Microbes of interest, but are not limited to, gram positive bacilli, e.g. Clostridia sp., e.g. *C. tetani, C. botulinum*; Corynebacterium sp., e.g. *C. diptheriae*; Staphylococcus sp., e.g. *S. aureus, S. epidermidis*; Streptococcus sp., e.g. *S. pyogenes, S. pneumoniae, S. agalactiae*. Gram negative bacteria include Citrobacter sp.; Enterobacter sp.; Escherichia sp., e.g. *E. coli*; Klebsiella sp.; Morganella sp.; Proteus sp.; Providencia sp.; Salmonella sp., e.g. *S. typhi, S. typhimurium*; Serratia sp.; Shigella sp.; Pseudomonas sp., e.g. *P. aeruginosa*; Yersinia sp., e.g. *Y. pestis, Y. pseudotuberculosis, Y enterocolitica*; Francisells sp.; Pasturella sp.; Vibrio sp., e.g. *V. cholerae, V. parahemolyticus*; Campylobacter sp., e.g. *C. jejuni*; Haemophilus sp., e.g. *H. influenzae, H. ducreyi*; Bordetella sp., e.g. *B. pertussis, B. bronchiseptica, B. parapertussis*; Brucella sp., Neisseria sp., e.g. *N. gonorrhoeae, N. meningitidis*, etc. Other bacteria include Legionella sp., e.g. *L. pneumophila*; Listeria sp., e.g. *L. monocytogenes*; Mycoplasma sp., e.g. *M. hominis, M. pneumoniae*; Mycobacterium sp., e.g. *M. tuberculosis, M. leprae*; Treponema sp., e.g. *T. pallidum*; Borrelia sp., e.g. *B. burgdorferi*; Leptospirae sp.; Rickettsia sp., e.g. *R. rickettsii, R. typhi*; Chlamydia sp., e.g. *C. trachomatis, C. pneumoniae, C. psittaci*; Helicobacter sp., e.g. *H. pylori*, etc.

Non baterial pathogens of interest include fungal and protozoan pathogens, e.g. Plasmodia sp., e.g. *P. falciparum*, Trypanosoma sp., e.g. *T. brucei*; shistosomes; Entaemoeba sp., Cryptococcus sp., Candida sp, e.g. *C. albicans*; etc.

Various methods for administration may be employed. The polypeptide formulation may be given orally, or may be injected intravascularly, subcutaneously, peritoneally, etc. Methods of administration by inhalation are well-known in the art. The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level. In many cases, oral administration will require a higher dose than if administered intravenously. The amide bonds, as well as the amino and carboxy termini, may be modified for greater stability on oral administration.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The granulysin may be systemic after administration or may be localized by the use of an implant that acts to retain the active dose at the site of implantation.

The compounds of the present invention can be administered alone, in combination with each other, or they can be used in combination with other known compounds (e.g., perforin, antibiotics, etc.) In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane,propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing granulysin is placed in proximity to the site of infection, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 $\mu$g to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like.

For preparing the liposomes, the procedure described by Kato et al. (1991) *J. Biol. Chem.* 266:3361 may be used. Briefly, the lipids and lumen composition containing the nucleic acids are combined in an appropriate aqueous medium, conveniently a saline medium where the total solids will be in the range of about 1–10 weight percent. After intense agitation for short periods of time, from about 5–60 sec., the tube is placed in a warm water bath, from about 25–40° C. and this cycle repeated from about 5–10 times. The composition is then sonicated for a convenient period of time, generally from about 1–10 sec. and may be further agitated by vortexing. The volume is then expanded by adding aqueous medium, generally increasing the volume by about from 1–2 fold, followed by shaking and cooling. This method allows for the incorporation into the lumen of high molecular weight molecules.

Formulations with Other Active Agents

For use in the subject methods, granulysin may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin. Cytokines may also be included in a granulysin formulation, e.g. interferon γ, tumor necrosis factor α, interleukin 12, etc.

As an alternative to antibiotics, granulysin may be formulated with perforin, or other agents that increase the ability of granulysin to act on intracellular organisms, e.g. *M. tb., C. trachomatis, R. ricketsii*, etc. Such agents may be perforin, granzymes, $CaPO_4$, etc. and will be added at a dose that is effective to increase granulysin killing of an intracellular pathogen by at least about 25%, usually at least about 50%.

Synthesis of Granulysin

Granulysin DNA sequences may be employed for synthesis of a complete granulysin protein, or polypeptide fragments thereof, particularly fragments corresponding to functional domains; binding sites; etc.; and including fusions of the subject polypeptides to other proteins or parts thereof. For expression, an expression cassette may be employed, providing for a transcriptional and translational initiation region, which may be inducible or constitutive, where the coding region is operably linked under the transcriptional control of the transcriptional initiation region, and a transcriptional and translational termination region. Various transcriptional initiation regions may be employed that are functional in the expression host.

The polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, or cells of a higher organism such as vertebrates, particularly mammals, e.g. COS 7 cells, may be used as the expression host cells. In some situations, it may be desirable to express the granulysin gene in mammalian cells, where the protein will benefit from native folding and post-translational modifications.

The polypeptides may be isolated and purified in accordance with conventional ways. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

The subject peptides may be prepared by synthesis. Various commercial synthetic apparatuses are available, for example automated synthesizers by Applied Biosystems Inc., Foster City, Calif., Beckman, etc. By using synthesizers, naturally occurring amino acids may be substituted with unnatural amino acids, particularly diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

For the most part, the peptides of the subject invention will employ the amino acids naturally found in granulysin, except as specifically indicated. However, as is well known, the contacts from a peptide do not involve all the amino acids, but only those amino acids which are involved with the conformation of the reciprocal binding member. Therefore, significant latitude is permitted with intervening amino acids, which are not involved with the contact points and are of a size and polar nature, so as not to significantly change the orientation of the amino acids involved in contacts.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like. Alternatively, one may provide for a wide variety of labels, as described previously, including ligands for binding to antibodies or natural receptors, where the peptides may be bound to a support or, alternatively, to another molecule.

Drug Screening Assays

Drug screening assays may be used to identify bioactive agents that mimic granulysin activity in microbial killing. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified granulysin protein may also be used for determination of three-dimensional crystal structure, which can be used for modeling intermolecular interactions, etc.

The term "agent" as used herein describes any molecule, e.g. protein or pharmaceutical, with the capability of mimicking or modulating the microbicidal activity of granulysin. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of infection. Depending upon the manner of introduction, the compounds may be formulated in a variety of ways. The concentration of therapeutically active compound in the formulation may vary from about 0.1–100 wt.%.

EXPERIMENTAL

Material and Methods

Purification of granulysin. A polyhistidine tagged recombinant 9 kD granulysin was produced in E. coli BL21 (DE3) using the kanamycin selective pET28a vector (Novagen). The protein coding region of granulysin cDNA, starting at the glycine at residue 48 of the 519 message and continuing through the arginine residue 121, was fused to the pET28a encoded amino-terminal polyhistidine sequence at the Nde 1 site. The recombinant proteins were expressed and purified under denaturing conditions as described (Pena paper). Preparations of recombinant granulysin were separated on SDS gel and silver-staining of proteins showed a single band. Purity of the preparation was additionally confirmed by ion spray mass spectroscopy which revealed the presence of a single peptide of 9.071 kDa, correlating with the predicted molecular mass of granulysin.

CFU-determination of bacteria and fungi. The CFU-assay for bacteria and fungi was performed as previously described. (Porter, Infect. Immun., 1997). Microorganisms and granulysin were mixed and coincubated at 37° C. for three hours in the presence of 10 mM $PO_4$ pH 7.4 with 0.03% Trypticase Soy Broth (TSB, Becton-Dickinson) for bacteria or 0.03% Sabouraud Dextrose Broth (SAB, Difco) for fungi in a final volume of 50 μl. Following incubation the samples were diluted 1:100 in ice-cold 10 mM $PO_4$ and spread on Trypticase Soy Agar or Sabouraud Dextrose Agar plates (Clinical Standard Laboratories Rancho Domingez, Calif.) with a spiral plater (Spiral Systems, Cincinatti, Ohio.), which delivers a defined volume per area and thus allows precise counts of microbial colonies.

Radial Diffusion. The agar radial diffusion assay was performed as previously described (Lehrer, R. I. et al. [1991]. Ultrasensitive Assays for endogenous antimicrobial polypeptides. J Immunol Methods 137:167–73). A bacterial-agar layer was prepared by adding $4 \times 10^6$ CFU/ml to 10 ml of a 3% agarose solution with 0.03% TSB. 3 mm wells were punched into the underlay, and 5 μl of granulysin dilution were allowed to diffuse into the agar for three hours at 37° C. 10 ml of a 6% TSB 3% agarose was overlayed and plates were incubated overnight. The clear zone diameter in the microbial carpet was measured.

Quantification of Leishmania major. 20,000 stationary phase L. major promastigotes were incubated with various concentrations of granulysin or diluent. After 48 hrs. the number of live parasites was determined by limiting dilution analysis. 10-fold serial dilutions were seeded into 96 well plates with Novy-Nicolle-MacNeal blood agar slants and the number of parasites was calculated by applying Poisson statistics and $\chi^2$-minimization (Stenger, JEM 1995).

Western Blot for granulysin. M. tuberculosis-specific, CD1 restricted DN and CD8+ CTL were generated and cultured as described previously (Stenger, 1997). Granulysin protein was detected by pelleting CTL, lysing them in SDS sample-buffer and separating proteins on 15% SDS-PAGE gels. Proteins were then transferred to nitrocellulose membranes. To ensure equal loading, the protein concentration was initially determined spectrophotometrically and confirmed by staining the nitrocellulose membranes with Ponceau red. Granulysin protein was detected using 519/GST rabbit serum (1/1000) followed by horseradish peroxidase-conjugated secondary Abs. Immundetection was performed using enhanced chemiluminescence following the manufacturer's guidelines.

Immunostaining for granulysin. CTL were immobilized on poly-$_L$-lysine slides, fixed with 4% paraformaldehyde and incubated with a permeabilization/blockingsolution (5% human serum, 5% goat serum, 0.1% TritonX, 0.01% saponin, 1% nonfat dry milk). Cells were stained with a monoclonal goat anti-mouse antibody (DH2, 5 μg/ml) and detected with a FITC-conjugated goat-anti mouse antibody.

Growth of M. tuberculosis. M. tuberculosis (virulent strain H37Rv) was grown in suspension with constant, gentle rotation in roller bottles containing Middlebrook 7H9 broth (Difco Detroit, Mich.) supplemented with glycerol, 0.05% Tween-80 (Sigma, St. Louis, Mo.) and 10% Middlebrook OADC enrichment (Difco). Aliquots from logarithmically growing cultures were frozen in PBS containing 10% glycerol, and representative vials were thawed and enumerated for viable colony forming units on Middlebrook 7H11 plates. Comparison of microscope counts of mycobacteria and their growth on agar plates revealed a viability of the bacteria above 90%. Since clumping of mycobacteria is a common problem which can influence the validity and reproducibility of the experiments we undertook several precautions to minimize clumps. (1) Culture conditions (rotation, Tween) were chosen to support the growth of single cell suspensions. (2) Prior to in vitro infection M. tuberculosis bacilli were sonicated to disrupt small aggregates of bacteria. (3) The MOI was selected such that there were only 2–3 bacilli per APC. (4) At the conclusion of every assay an aliquot of infected cells was stained with auramine rhodamine to confirm the absence of any clumps.

Colony forming units for M. tuberculosis. To assess the bactericidal activity of granulysin against extracellular M. tuberculosis 10,000 bacteria were incubated in 7H9 Middlebrook medium supplemented with 10 % OADC in triplicates on a 96 well culture plate. Granulysin, diluted in 0.01% acetic acid or diluent alone were added at the concentrations indicated. After 48 hrs. surviving M. tuberculosis were enumerated by plating 10-fold dilutions (in 7H9+10% OADC) of the bacterial suspension on 7H10 Middlebrookagar plates. Plates were incubated at 37° C. for 14 to 21 days in 5% $CO_2$.

Intracellular killing of M. tuberculosis. PBMCs from healthy donors were treated with GM-CSF (200 U/ml) and IL-4 (100 U/ml) for 3 days. Adherent cells were detached by treatment with 1 mM EDTA (Sigma) and replated in 6-well plates at a density of $3 \times 10^6$ cells per well. Adherent monolayers were infected with live M. tuberculosis at a multiplicity of infection (MOI) of 5:1. After 4 hrs. non-phagocytosed bacteria were removed by extensive washing. Macrophages were then detached and the efficiency of infection determined by staining an aliquot with auramine/rhodamine (3.77±0.32 bacteria/cell, 83±4% cells infected). The microscopic evaluation of infected macrophages under the fluorescence microscope confirmed the absence of any mycobacterial aggregates. Cell viability of infected APC was determined by measuring the enzymatic activity of lactate dehydrogenase in the culture supernatants (CytoTox 96, Promega, Madison, Wis.) and was >95% in all experiments. Infected cells were incubated with increasing concentrations of granulysin for in RPMI+10% FCS. Experiments involving treatment of cells with perforin required slightly modified culture conditions. Cells were cultured in RPMI+1% fatty acid free BSA and Hepes buffer supplemented with 2.5 mM $CaCl_2$. 48 hrs. after treatment cells were lysed with 0.1% saponin to release intracellular bacteria. For the determination of mycobacterial viability, tenfold dilutions of the lysate were plated in duplicates on 7H11 agar plates. Colony forming units were counted after a three week incubation.

Killing of intracellular *M. tuberculosis* by a flu peptide specific line. To determine whether killing of intracellular *M. tuberculosis* by $CD8^+$ T cells requires the presence of cytotoxic granules we pretreated flu peptide specific MHC class I restricted CTL with the degranulating agent strontium as described. CTL were coincubated with flu peptide pulsed macrophages, that were infected with live *M. tuberculosis* (MOI 5:1, 4 hrs). Some cells were pretreated with oATP, which is an irreversible inhibitor of extracellular ATP. After 18 hrs. cells were lysed with saponin to release intracellular bacteria. For the determination of mycobacterial viability, fivefold dilutions of the lysate were plated in duplicates on 7H11 agar plates. Colony forming units were counted after a three week incubation.

Results

The antimicrobial activity of granulysin against a spectrum of infectious agents was evaluated. Culture conditions were adapted for the specific growth requirements of each organism and growth inhibition induced by recombinant granulysin was initially screened by radial diffusion assay and confirmed by colony forming unit assay, data shown in FIG. 1. Granulysin showed potent antibacterial activity in the micromolar range against a variety of gram positive and gram negative bacteria, causing a three order magnitude reduction in CFU of *Salmonella typhimurium, Listeria monocytogenes, Escherichia coli* and *Staphylococcus aureus*. Granulysin also effectively kills fungi and parasites, including *Cryptococccus neoformans, Candida albicans* and *Leishmania major* but to a more variable extent. The broad antimicrobial spectrum of granulysin is reminiscent of defensins, which are nonspecifically released from cytoplasmic granules of polymorphnuclear leukocytes to kill phagocytosed pathogens.

A unique aspect of granulysin is its localization to cytotoxic granules of T cells, thereby restricting their release only upon antigen stimulation. We recently demonstrated the existence of two subsets of CTL, which differed in phenotype, cytotoxic effector pathway and antimicrobial activity. $CD8^+$ CTL lysed *Mycobacterium tuberculosis* infected macrophages by a Fas independent, cytotoxic granule-dependent mechanism that resulted in killing of the intracellular pathogen. In contrast, the cytotoxicity of $CD4^- CD8^-$ (double negative, DN) T cells was mediated by Fas/Fas ligand interaction and did not result in growth inhibition of the mycobacteria. The presence of granulysin in these two populations was therefore investigated. By Western blot analysis and immunolabeling, granulysin was detected in $CD8^+$ CTL but not DN CTL. Immunostaining of $CD8^+$ CTL for granluysin revealed a punctate pattern, indicative of granule localization. Perforin which is known to be present in cytoplasmic granules was similarly identified in $CD8^+$ CTL but was not found in DN CTL. Killing of intracellular *M. tuberculosis* by $CD8^+$ CTL was dependent on the presence of granule components since degranulation of the CTL by $Sr^{++}$ abrogated the antibacterial effect. The microbicidal activity correlated with the disappearance of granulysin from the cells. Intracellular killing of mycobacteria was not due to ATP, a granule constituent which has been implicated in the killing of *M. tuberculosis*.

Figure 2A:
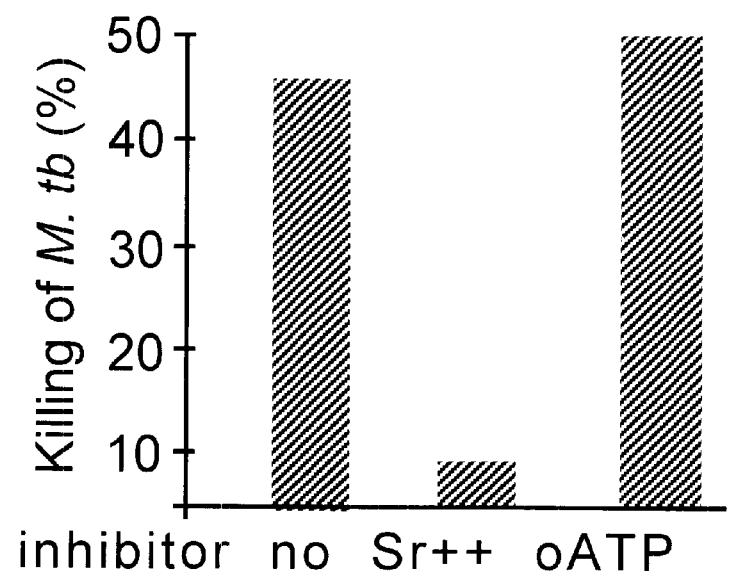
FIGS. 2A and 2B show the killing of intracellular *M. tuberculosis* by granulysin+ CTL in the presence or absence of the inhibitors $Sr^{++}$ (a degranulating agent) and ATP.
Figure 2B:
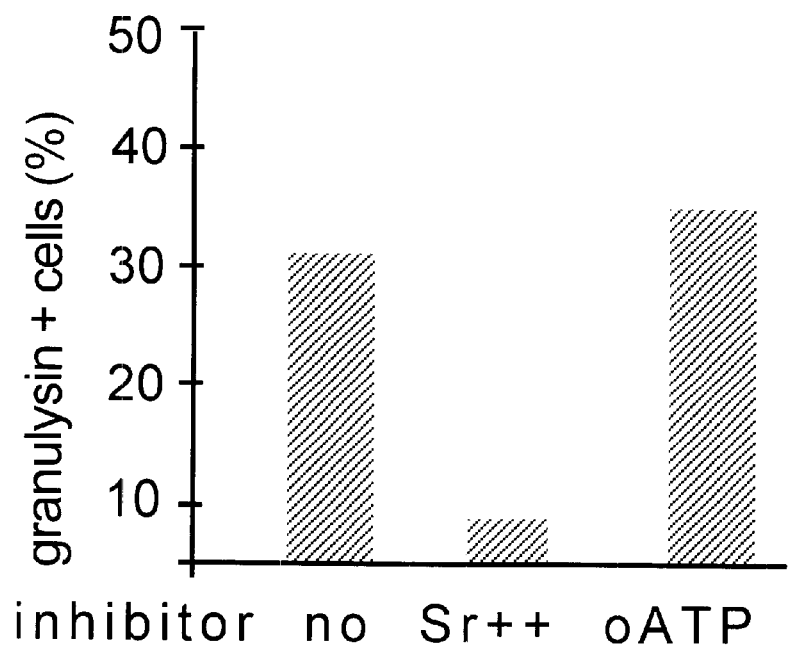
Figure 4B:
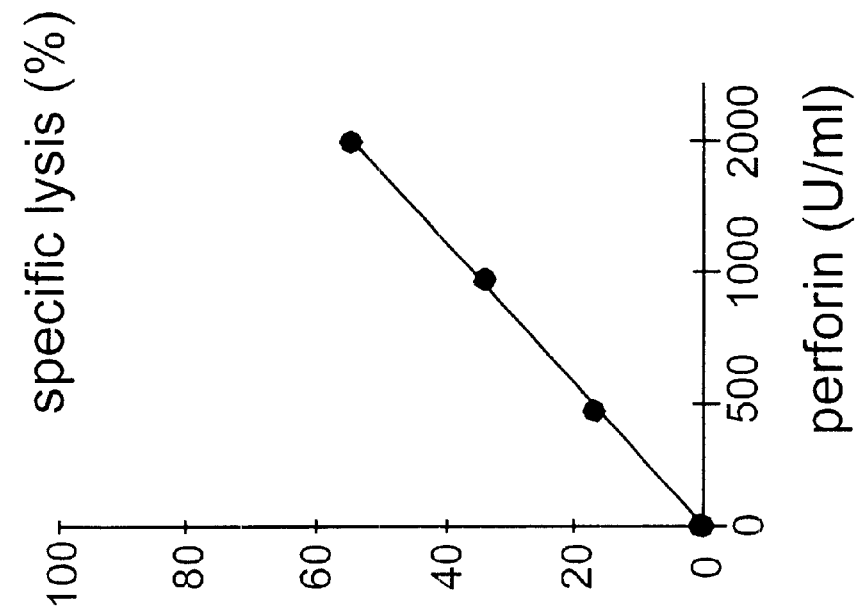
FIGS. 4A and 4B are graphs depicting the lytic activity of granulysin and perforin against human monocytes infected with *M. tuberculosis*.
Figure 4A:
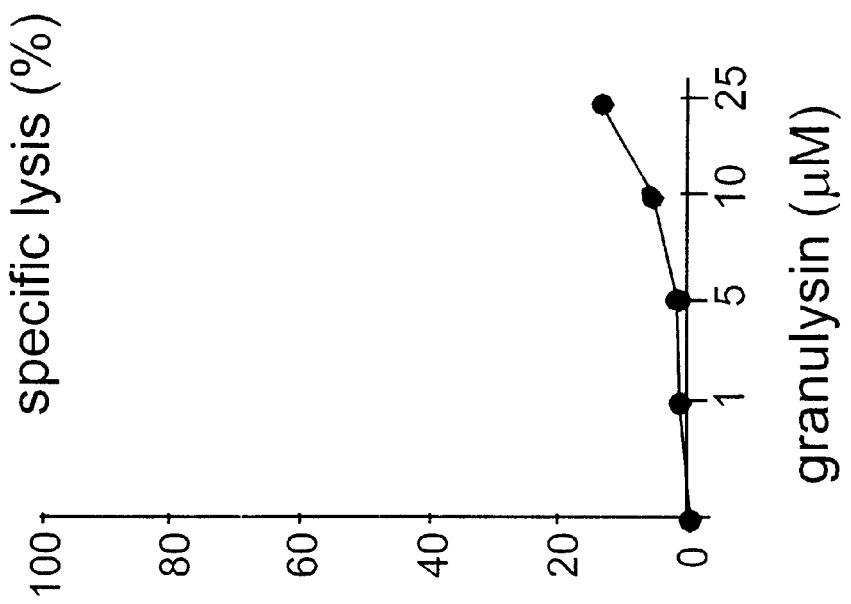
Figure 5:
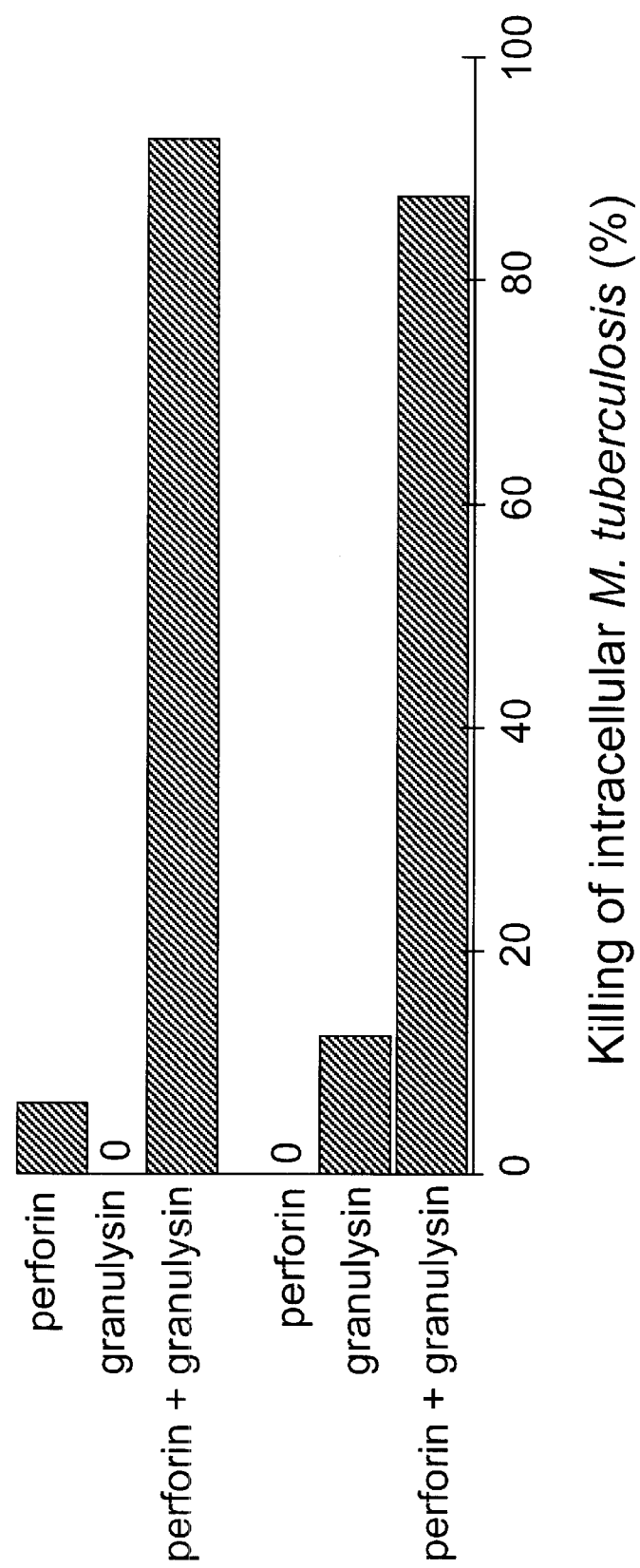
FIG. 5 is a bar graph depicting the synergistic action of perforin plus granulysin in the elimination of *M. tuberculosis*.

These data suggested that the effector function of granulysin might contribute to the ability of CTL to kill *M. tuberculosis*. This was examined by culturing *M. tuberculosis* in 7H9 media in the presence of various concentrations of granulysin (FIG. 2). In four experiments, granulysin killed *M. tuberculosis* in a dose dependent mannerto an extent similar for *Leishmania major* and *Candida albicans*. Up to 90% of the bacteria were killed in 48 hrs, representing almost a log reduction in the number of CFU. However, no antibacterial activity was detected when granulysin was added to *M. tuberculosis*-infected monocytes.

The inability of granulysin to kill intracellular *M. tuberculosis* might be due to its failure to gain access to intracellular compartment in which mycobacteria reside. Experiments were therefore designed to compare relative activities of granulysin and perforin in lysing human monocytes (FIG. 3). Granulysin, when added in a concentration range which efficiently killed extracellular bacteria, showed poor lytic activity against human monocytes infected with *M. tuberculosis*. In contrast, perforin which is known to lyse various hematopoietic targets, demonstrated significant lytic activity against identically infected monocytes.

Perforin and granulysin are both present in cytotoxic granules, raising the possibility that they act in concert in delivering the lethal hit both to the cell and the intracellular pathogen. Neither perforin nor granulysin alone effectively killed intracellular *M. tuberculosis*. However, perforin plus granulysin were synergistic, eliminating 90% of the mycobacteria.

These findings suggest a novel pathway by which T cells directly contribute to the death of microbial pathogens, specifically microorganisms residing in intracellular compartments. Perforin polymerizes on the target cell membrane and induces a non-selective pore that has been suggested to be responsible for lysis. Granulysin may enter the cell through this pore and destroy the invader. Alternatively, granulysin may enter target cells via endocytosis and be released from endosomes by perforin. This perforin-granulysin microbicidal pathway is likely to complement other mechanisms by which monocytes kill pathogens, including nitric oxide and oxygen free radical generation.

The presence of granulysin in NK cells and of related peptides in cytoplasmic granules of *Entamoeba histolytica* suggest that the saposin-like protein family represents an ancient yet preserved form of antimicrobial host defense, part of the innate immune response. The importance of this pathway is reflected by the presence of granulysin and other family members in CTL, indicating that the adaptive immune response has evolved to include anti-microbial peptides for effective immunity. These data provide evidence for a novel pathway by which T cells can directly mediate immunityto microbial infection.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for reducing the number of viable cells in a bacterial population, the method comprising:

contacting said bacterial population with an effective dose of an antimicrobial formulation comprising granulysin as an active agent; wherein said effective dose has been determined by the method of contacting bacterial cells with granulysin; identifying a reduction in the number of viable bacterial cells after exposure to said granulysin; and correlating the concentration of granulysin with the reduction in the number of viable cells;

wherein the number of viable cells in said bacterial population is reduced.

2. A method according to claim 1, wherein the number of viable cells in said microbial population is reduced by at least 90%.

3. A method according to claim 1, wherein the number of viable cells in said microbial population is reduced by at least 99%.

4. A method for reducing the number of viable cells in a fungal pathogen population, the method comprising:

contacting said fungal pathogen population with an effective dose of an antimicrobial formulation comprising granulysin as an active agent; wherein said effective dose has been determined by the method of contacting fungal pathogen cells with granulysin, identifying a reduction in the number of viable fungal pathogen cells after exposure to said granulysin, and correlating the concentration of granulysin with the reduction in the number of viable cells;

wherein the number of viable cells in said fungal pathogen population is reduced.

5. A method according to claim 1, wherein said contacting comprises administration in vivo to an infected host.

6. A method according to claim 1, wherein said contacting comprises administration in vitro.

7. A method according to claim 1, wherein said granulysin is human granulysin.

8. A method according to claim 7, wherein said human granulysin comprises the amino acid sequence as set forth in SEQ ID NO:1.

9. A method according to claim 1, wherein said antimicrobial formulation further comprises a second antimicrobial agent.

10. A method according to claim 9, wherein said second antimicrobial agent is an antibiotic.

11. A method according to claim 9, wherein said second antimicrobial agent is perforin.

12. A method according to claim 11, wherein said microbial population comprises *Mycobacterium tuberculae.*

13. An antimicrobial pharmaceutical composition, comprising:

granulysin in an amount effective to reduce the number of viable cells in a microbial population; and a pharmaceutically acceptable carrier.

14. An antimicrobial pharmaceutical composition according to claim 13, wherein said amount is effective to reduce the number of viable cells in a microbial population by at least about 90%.

15. An antimicrobial pharmaceutical composition according to claim 13, wherein said amount is effective to reduce the number of viable cells in a microbial population by at least about 99%.

16. An antimicrobial pharmaceutical composition according to claim 13, further comprising a second antimicrobial agent.

17. An antimicrobial pharmaceutical composition according to claim 16, wherein said second antimicrobial agent is an antibiotic.

18. An antimicrobial pharmaceutical composition according to claim 16, wherein said second antimicrobial agent is perforin.

* * * * *

UNITED STATES PATENT AND TRADEMARK OFFICE
CERTIFICATE OF CORRECTION

PATENT NO.     : 6,485,928 B2  
DATED          : November 26, 2002  
INVENTOR(S)    : Stenger, Steffen et al.

It is certified that error appears in the above-identified patent and that said Letters Patent is hereby corrected as shown below:

<u>Title page,</u>  
Item [75], please replace the "Inventors" as follows:

-- Steffen Stenger, Erlangen (DE);  
  Robert L. Modlin, Sherman Oaks, CA (US);  
  Dennis Alan Hanson, Mountain View, CA (US);  
  Alan M. Krensky, Stanford, CA (US)  
  Susan Valerie Jennings, San Diego, CA (US & CH); --

Signed and Sealed this

Twentieth Day of May, 2003

JAMES E. ROGAN  
*Director of the United States Patent and Trademark Office*

UNITED STATES PATENT AND TRADEMARK OFFICE
CERTIFICATE OF CORRECTION

PATENT NO.   : 6,485,928 B2
DATED        : November 26, 2002
INVENTOR(S)  : Stenger, Steffen et al.

It is certified that error appears in the above-identified patent and that said Letters Patent is hereby corrected as shown below:

<u>Column 1,</u>
Line 4, please replace the first paragraph with the revised paragraph that reads:

-- This invention was made with Government support under Grant No. AI43348 and DK35008 awarded by the National Institutes of Health. The Government may have certain rights in this invention. --

Signed and Sealed this

First Day of July, 2003

JAMES E. ROGAN
*Director of the United States Patent and Trademark Office*

SEQUENCE LISTING

<160> NUMBER OF SEQ ID NOS: 4

<210> SEQ ID NO 1
<211> LENGTH: 74
<212> TYPE: PRT
<213> ORGANISM: H. sapiens

<400> SEQUENCE: 1

Gly Arg Asp Tyr Arg Thr Cys Leu Thr Ile Val Gln Lys Leu Lys Lys
 1               5                  10                  15

Met Val Asp Lys Pro Thr Gln Arg Ser Val Ser Asn Ala Ala Thr Arg
                20                  25                  30

Val Cys Arg Thr Gly Arg Ser Arg Trp Arg Asp Val Cys Arg Asn Phe
            35                  40                  45

Met Arg Arg Tyr Gln Ser Arg Val Ile Gln Gly Leu Val Ala Gly Glu
        50                  55                  60

Thr Ala Gln Gln Ile Cys Glu Asp Leu Arg
65                  70

<210> SEQ ID NO 2
<211> LENGTH: 129
<212> TYPE: PRT
<213> ORGANISM: H. sapiens

<400> SEQUENCE: 2

Met Glu Gly Leu Val Phe Ser Arg Leu Ser Pro Glu Tyr Tyr Asp Pro
 1               5                  10                  15

Ala Arg Ala His Leu Arg Asp Gly Glu Lys Ser Cys Pro Cys Gly Gln
                20                  25                  30

Glu Gly Pro Gln Gly Asp Leu Leu Thr Lys Thr Gln Glu Leu Gly Arg
            35                  40                  45

Asp Tyr Arg Thr Cys Leu Thr Ile Val Gln Lys Leu Lys Lys Met Val
        50                  55                  60

Asp Lys Pro Thr Gln Arg Ser Val Ser Asn Ala Ala Thr Arg Val Cys
65                  70                  75                  80

Arg Thr Gly Arg Ser Arg Trp Arg Asp Val Cys Arg Asn Phe Met Arg
                85                  90                  95

Arg Tyr Gln Ser Arg Val Ile Gln Gly Leu Val Ala Gly Glu Thr Ala
               100                 105                 110

Gln Gln Ile Cys Glu Asp Leu Arg Leu Cys Ile Pro Ser Thr Gly Pro
           115                 120                 125

Leu

<210> SEQ ID NO 3
<211> LENGTH: 145
<212> TYPE: PRT
<213> ORGANISM: H. sapiens

<400> SEQUENCE: 3

Met Ala Thr Trp Ala Leu Leu Leu Ala Ala Met Leu Leu Gly Asn
 1               5                  10                  15

Pro Gly Leu Val Phe Ser Arg Leu Ser Pro Glu Tyr Tyr Asp Leu Ala
                20                  25                  30

Arg Ala His Leu Arg Asp Glu Glu Lys Ser Cys Pro Cys Leu Ala Gln
            35                  40                  45

Glu Gly Pro Gln Gly Asp Leu Leu Thr Lys Thr Gln Glu Leu Gly Arg

-continued

```
                 50                  55                  60
Asp Tyr Arg Thr Cys Leu Thr Ile Val Gln Lys Leu Lys Lys Met Val
 65                  70                  75                  80

Asp Lys Pro Thr Gln Arg Ser Val Ser Asn Ala Ala Thr Arg Val Cys
                 85                  90                  95

Arg Thr Gly Arg Ser Arg Trp Arg Asp Val Cys Arg Asn Phe Met Arg
                100                 105                 110

Arg Tyr Gln Ser Arg Val Thr Gln Gly Leu Val Ala Gly Glu Thr Ala
                115                 120                 125

Gln Gln Ile Cys Glu Asp Leu Arg Leu Cys Ile Pro Ser Thr Gly Pro
130                 135                 140

Leu
145

<210> SEQ ID NO 4
<211> LENGTH: 172
<212> TYPE: PRT
<213> ORGANISM: H. sapiens

<400> SEQUENCE: 4

Met Ala Thr Trp Ala Leu Leu Leu Leu Ala Ala Met Leu Leu Gly Asn
 1                   5                  10                  15

Pro Gly Leu Glu Val Ser Val Ser Pro Lys Gly Lys Asn Thr Ser Gly
                 20                  25                  30

Arg Glu Ser Gly Phe Gly Trp Ala Ile Trp Met Glu Gly Leu Val Phe
                 35                  40                  45

Ser Arg Leu Ser Pro Glu Tyr Tyr Asp Leu Ala Arg Ala His Leu Arg
                 50                  55                  60

Asp Glu Glu Lys Ser Cys Pro Cys Leu Ala Gln Glu Gly Pro Gln Gly
 65                  70                  75                  80

Asp Leu Leu Thr Lys Thr Gln Glu Leu Gly Arg Asp Tyr Arg Thr Cys
                 85                  90                  95

Leu Thr Ile Val Gln Lys Leu Lys Lys Met Val Asp Lys Pro Thr Gln
                100                 105                 110

Arg Ser Val Ser Asn Ala Ala Thr Arg Val Cys Arg Thr Gly Arg Ser
                115                 120                 125

Arg Trp Arg Asp Val Cys Arg Asn Phe Met Arg Arg Tyr Gln Ser Arg
                130                 135                 140

Val Ile Gln Gly Leu Val Ala Gly Glu Thr Ala Gln Gln Ile Cys Glu
145                 150                 155                 160

Asp Leu Arg Leu Cys Ile Pro Ser Thr Gly Pro Leu
                165                 170
```